United States Patent
Seyfried

(10) Patent No.: US 7,482,600 B2
(45) Date of Patent: Jan. 27, 2009

(54) METHOD FOR INVESTIGATING TRANSPORT PROCESSES

(75) Inventor: Volker Seyfried, Nussloch (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 11/225,809

(22) Filed: Sep. 13, 2005

(65) Prior Publication Data

US 2006/0054800 A1    Mar. 16, 2006

(30) Foreign Application Priority Data

Sep. 13, 2004   (DE) ................. 10 2004 044 626

(51) Int. Cl.
*G21H 3/02*    (2006.01)
(52) U.S. Cl. ................ 250/459.1; 356/318; 436/52
(58) Field of Classification Search ............ 250/459.1, 250/458.1; 436/52; 356/318
See application file for complete search history.

(56) References Cited

U.S. PATENT DOCUMENTS

| | | | | |
|---|---|---|---|---|
| 5,159,352 A * | 10/1992 | Ferla et al. ................ 347/248 |
| 5,304,810 A | 4/1994 | Amos |
| 5,731,588 A * | 3/1998 | Hell et al. ............... 250/458.1 |
| 5,817,462 A * | 10/1998 | Garini et al. ................ 435/6 |
| 6,094,300 A * | 7/2000 | Kashima et al. ............ 359/385 |
| 6,462,345 B1 | 10/2002 | Simon et al. |
| 6,519,355 B2 * | 2/2003 | Nelson ..................... 382/133 |
| 6,630,680 B2 | 10/2003 | Hakamata et al. |
| 6,650,357 B1 * | 11/2003 | Richardson ................ 348/80 |
| 6,677,566 B2 * | 1/2004 | Knebel et al. ............ 250/201.3 |
| 6,710,855 B2 * | 3/2004 | Shiraishi ................... 355/67 |
| 2001/0046054 A1 * | 11/2001 | Zeylikovich et al. ........ 356/497 |
| 2002/0027203 A1 * | 3/2002 | Engelhardt et al. ....... 250/459.1 |
| 2003/0152271 A1 * | 8/2003 | Tsujino et al. ............. 382/190 |
| 2003/0197924 A1 * | 10/2003 | Nakata ..................... 359/368 |
| 2004/0042007 A1 | 3/2004 | Oslpchuk et al. |
| 2004/0091259 A1 * | 5/2004 | Hanzawa ................... 396/534 |
| 2004/0178356 A1 | 9/2004 | Natori |
| 2004/0243113 A1 * | 12/2004 | Sugiura et al. ................ 606/5 |
| 2005/0109087 A1 * | 5/2005 | Robb et al. ............... 73/53.01 |
| 2005/0275839 A1 * | 12/2005 | Robinson et al. ........... 356/318 |
| 2006/0011812 A1 * | 1/2006 | Wolleschensky et al. .. 250/208.1 |
| 2006/0068371 A1 * | 3/2006 | Ortyn et al. .................... 435/4 |

FOREIGN PATENT DOCUMENTS

DE      198 29 981      1/2000
JP      2004-110 017 A  4/2004

* cited by examiner

*Primary Examiner*—Stephen Yam
(74) *Attorney, Agent, or Firm*—Houston Eliseeva LLP

(57) ABSTRACT

A method for investigating transport processes in a preferably biological specimen, a laser light beam (2, 3) being guided by means of a scanning apparatus line by line over the specimen within definable specimen regions, and the light proceeding from the specimen being detected by means of a detection apparatus, is characterized, in the interest of the capability of investigating, with high accuracy, processes within the specimen that proceed on a short time scale, in that both an image production light beam (5) for the purpose of observing the specimen and a manipulation light beam (4) for the purpose of manipulating the specimen are used as the laser light beam (2, 3), the image production light beam (5) preceding the manipulation light beam (4) in such a way that pixels of the specimen not yet manipulated by the manipulation light beam (4) are illuminated with the image production light beam (5).

21 Claims, 4 Drawing Sheets

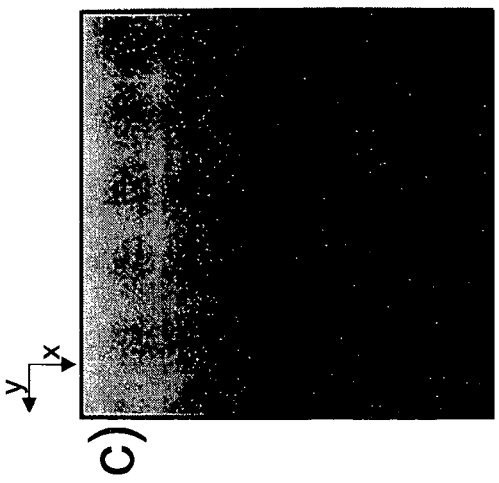
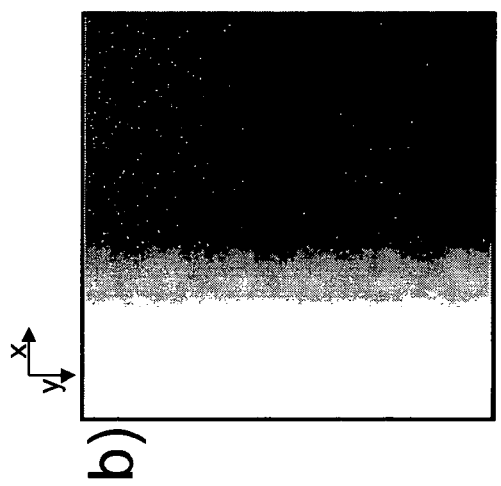
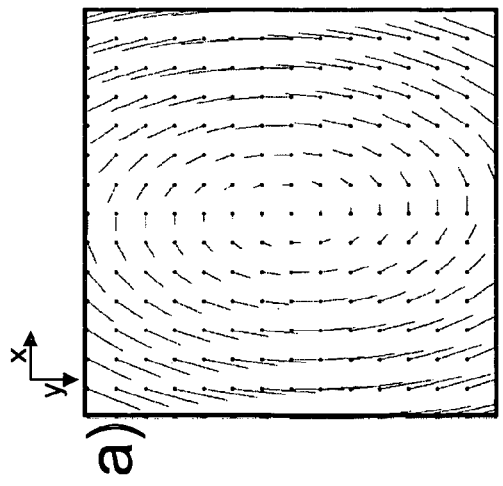
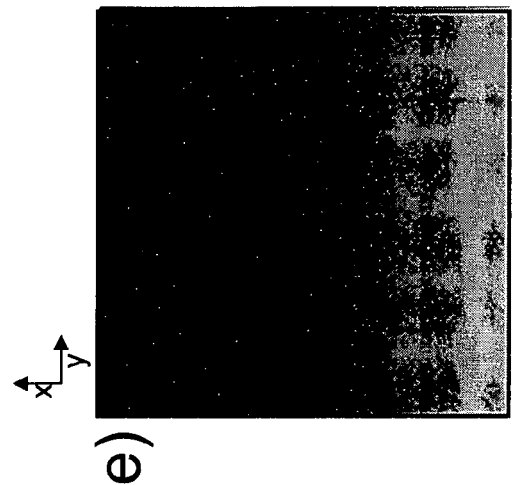
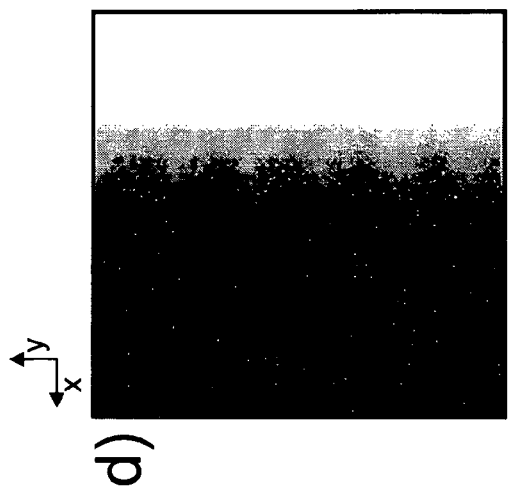
Fig. 3

METHOD FOR INVESTIGATING TRANSPORT PROCESSES

RELATED APPLICATIONS

This application claims priority to German patent application number 10 2004 044 626.1, filed Sep. 13, 2004, which is incorporated herein by reference in its entirety.

FIELD OF THE INVENTION

The invention concerns a method for investigating transport processes in a preferably biological specimen, a laser light beam being guided by means of a scanning apparatus line by line over the specimen within definable specimen regions, and the light proceeding from the specimen being detected by means of a detection apparatus.

BACKGROUND OF THE INVENTION

Methods of the kind under discussion here have been known in practical use for some time in a variety of embodiments. Of the known methods, only fluorescence recovery after photobleaching (FRAP), fluorescence loss in photobleaching (FLIP), or photoactivation will be mentioned by way of example. It is characteristic of these methods that a definable region of interest (ROI) is illuminated in a particular fashion. In FRAP, FLIP, or photoactivation experiments, this so-called manipulation illumination is characterized, for example, by a particularly high brightness. In the corresponding inverse experiments (inverse FRAP, inverse FLIP, inverse photoactivation), on the other hand, a particularly dark manipulation illumination is selected. Also known are methods in which the illumination during normal imaging and the manipulation illumination are distinguished from one another by their respective spectral compositions.

The purpose of the manipulation illumination is to set in motion certain processes in the specimen being investigated; this can be, for example, bleaching or photoactivation of a fluorophore. Also conceivable is a reorganization within a fluorophore. These processes can result in changes in the spectral properties, or other detectable changes.

By way of a locally differing selected manipulation illumination, local properties can be imparted to the specimen so that, for example, after manipulation illumination certain parts of cells have fluorophores that are visible particularly well or particularly poorly. The local properties imparted to the specimen can then be made visible in a confocal microscope.

A redistribution of the fluorophores takes place as a result of transport processes in the interior of the specimen, for example inside cells. In many cases the transport processes ultimately result in a more or less homogeneous distribution of the fluorophores. The behavior over time of these processes can be made visible with the aid of microscopic images, allowing conclusions as to the transport processes in the specimen.

Conventional experiments of the kind described above are generally carried out in such a way that the specimen is first scanned, once or repeatedly, with a laser light beam for the manipulation illumination. In a subsequent step, the specimen is then scanned for the actual image acquisition. The result obtained therefrom is a series of images at different time intervals. At a typical image acquisition rate, which is on the order of 1 to 100 frames per second, the time interval between two successive images is 10 ms to 1 second. It is extremely problematic in this context that diffusion processes in biological specimens generally proceed much more quickly. A fluorophore typically moves in a few microseconds out of the focus of a confocal microscope. Such snapshots consequently allow only extremely poor investigation of local properties of transport processes, for example local flow directions, barriers, etc., since a local excitation effected by the manipulation illumination propagates too greatly between two successive images. For image production, for example for color depiction of regions of the specimen having different transport properties, the known methods are, for the reasons described, quite entirely unsuitable.

The so-called "volume effect" moreover causes additional problems for specimen investigation. The volume effect becomes apparent by the fact that transport processes also take place physically out of and into the image plane of a confocal microscope. Because the regions of the specimen located outside (i.e. above and below) the image plane are not accessible to observation, it is extremely difficult to interpret measured diffusion constants or other local conditions. For example, a local transport barrier in the image plane is not visible if the transport process overcomes that barrier by bypassing it through the volume located above or below it. Signal quality is also negatively affected by the volume effect, since manipulated fluorophores migrate relatively quickly into the volume above and below the image plane that is inaccessible to observation.

To circumvent the problems associated with the volume effect, measurements for the investigation of transport processes in specimens are often performed with the confocal microscope pinhole open. This degrades the resolution in the laser beam direction, and a projected image of the specimen, instead of a defined section of the specimen, is acquired. This allows better interpretation of the data that are obtained, but at the same time the essential advantages of a confocal microscope—such as high resolution, flare suppression, etc.—must be sacrificed.

SUMMARY OF THE INVENTION

It is now the object of the present invention to describe a method for investigating transport processes of the kind cited initially with which, in particular, processes within the specimen that proceed on a short time scale can also be investigated with high accuracy.

The method according to the present invention for investigating transport processes achieves the aforesaid object by way of the features of claim 1. According to the latter, such a method is characterized in that both an image production light beam for the purpose of observing the specimen and a manipulation light beam for the purpose of manipulating the specimen are used as the laser light beam, the image production light beam preceding the manipulation light beam in such a way that pixels of the specimen not yet manipulated by the manipulation light beam are illuminated with the image production light beam.

What has been recognized according to the present invention is firstly that the image acquisition rate of methods in which the specimen is scanned first with the manipulation illumination, and in a subsequent step for actual image acquisition, is too low for satisfactorily accurate investigation of transport processes that proceed rapidly, especially in biological specimens. The present invention proposes that definable regions of the specimen be illuminated by a laser light beam first for the purpose of observing the specimen and then for the purpose of manipulating the specimen. The consequence of the method according to the present invention is that only regions of the specimen that have not yet been exposed to any manipulation illumination are observed. The invention makes use, in this context, of the effect that after the manipulation illumination of definable specimen regions, transport processes take place which result, for example, in the transport of fluorophores into adjacent pixels. These can be sensed by the image production light beam, for example in the next line. Image production thus follows the manipulation illumination at an extremely short time interval, with the result that even rapidly proceeding transport processes are made accessible to observation.

Advantageously, each line of the specimen is swept twice by the laser light beam, the first illumination serving for image production and the second illumination for manipulation of the specimen. Once the manipulation light beam has influenced the specimen pixels swept by it, fluorophores are transported into adjacent pixels as a result of transport processes. Those fluorophores that are transported into the next image line that is imaged are then sensed by the image production light beam in the next line, and become visible in the image. This yields an image in which the only fluorophores visible are those that were transported in the direction of the next image line as a result of a transport process. If a Cartesian coordinate system is defined in which the specimen is scanned, for example, in the positive X direction, the measured image brightness then constitutes a direct indication of the local transport flow in the Y direction.

According to an alternative embodiment, each line of the specimen is swept by the laser light beam only once, the lines being used alternately for observation purposes and for manipulation purposes.

In the interest of simple evaluation of and a high information content in the acquired images, a fixed correlation in time between the image production illumination and the manipulation illumination of the specimen proves advantageous.

In the context of a further embodiment, provision is made for a separate laser light beam to be used respectively for image production and for manipulation of the specimen. In other words, a second laser light beam is used in addition to the laser light beam usually used for image production, and the two laser light beams can exhibit a fixed angle difference with respect to one another. This results in two illumination points at different locations on the specimen, which points possess a fixed physical distance from one another and scan the specimen synchronously with one another. The result of a fixed angle difference, whose magnitude can be defined in each case as a function of the specific application and the specific specimen properties, is that there is always a fixed distance in time between the image production light beam and the manipulation light beam of the previous line.

In particularly advantageous fashion, the investigation is carried out by means of a confocal microscope. Because the image is generated almost immediately after manipulation, and volume processes consequently play a subordinate role, all the advantages of the confocal microscope can be utilized. In particular, it is not necessary to perform the investigation with the confocal microscope pinhole open; in other words, it is possible to work with a high resolution in the laser beam direction in order to achieve highly accurate image production.

In the interest of a high degree of flexibility, provision can be made for the speed of the scanning apparatus to be adapted to the speed of the transport processes being investigated. The investigation can thereby be adapted to specimens having different properties and to different experimental situations, so that the most comprehensive information possible can always be obtained about the transport processes taking place in the respective specimen.

For efficient investigation, regions of particular interest in the specimen can be determined, and the manipulation illumination of the specimen can be confined to the regions of interest that are defined.

During the scanning operation, for example in the X direction, which is also referred to as an X scanning operation, the lines of the specimen can be illuminated continuously for the purpose of manipulation. For certain applications, on the other hand, it may be advantageous to alternately illuminate and not illuminate regions within a line. Manipulation illumination in a checkerboard-like pattern is, in particular, conceivable.

In the context of a more complex embodiment, provision can be made for a spectrally selective manipulation illumination of the specimen, so that different types of fluorophores in the specimen can be excited in controlled fashion. In the context of such an embodiment, it is additionally advantageous to design the detection apparatus in such a way that a spectrally sensitive detection of the light proceeding from the specimen is also possible.

To allow the most comprehensive information possible to be gathered regarding the transport processes taking place in the specimen, it is advantageous to acquire multiple images of the specimen, the individual images being rotated with respect to one another through a definable angle. The rotation of the image for another image acquisition can be implemented, for example, by means of an image rotator or by suitable activation of the scanning apparatus. From the acquired images, the transport flow in the interior of the specimen can then easily be calculated, for example, by determining the projection of the flow onto a fixed X or Y axis relative to the specimen, by suitable differentiation of the intensity values of the individual images. An alternative possibility is only to acquire one set of three images, for example for rotations of 0°, 120°, and 240°. The desired information can easily be ascertained by way of suitable linear combinations of the images. Appropriate techniques, including the associated correction methods, are well known in the context of quadrature encoders, and need not be explained in detail at this juncture.

In the interest of highly accurate measurement results, it is advantageous to apply suitable correction methods for the investigation. Both online corrections, in which the specimen is influenced during the measurement itself, and subsequent offline corrections, are possible. The correction methods used make it possible, for example, to take into account offsets, the enrichment of cells with photoactivated fluorophores over the course of the measurement sequence, or similar undesired effects.

The data obtained can be presented in multifarious ways, depending on the particular specific situation. A visualization of the measured data via color codings, vector diagrams, contour line graphs, or the like is particularly advantageous. It is furthermore possible to plot boundary lines and/or boundary surfaces in the acquired images on the basis of the measured data. The respective flow through the boundaries could additionally be indicated quantitatively. A representational identification of flow sources and/or flow sinks is likewise conceivable.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

There are various ways of advantageously embodying and refining the teaching of the present invention. The reader is referred, for that purpose, on the one hand to the claims subordinate to claim 1, and on the other hand to the explanation below of preferred exemplifying embodiments of the invention with reference to the drawings. In conjunction with the explanation of the preferred exemplifying embodiments of the invention with reference to the drawings, an explanation is also given of generally preferred embodiments and refinements of the teaching. In the drawings:

FIG. 3 schematically depicts images acquired with a method according to the present invention.

DETAILED DESCRIPTION OF THE PREFERRED EMBODIMENTS

Figure 1:
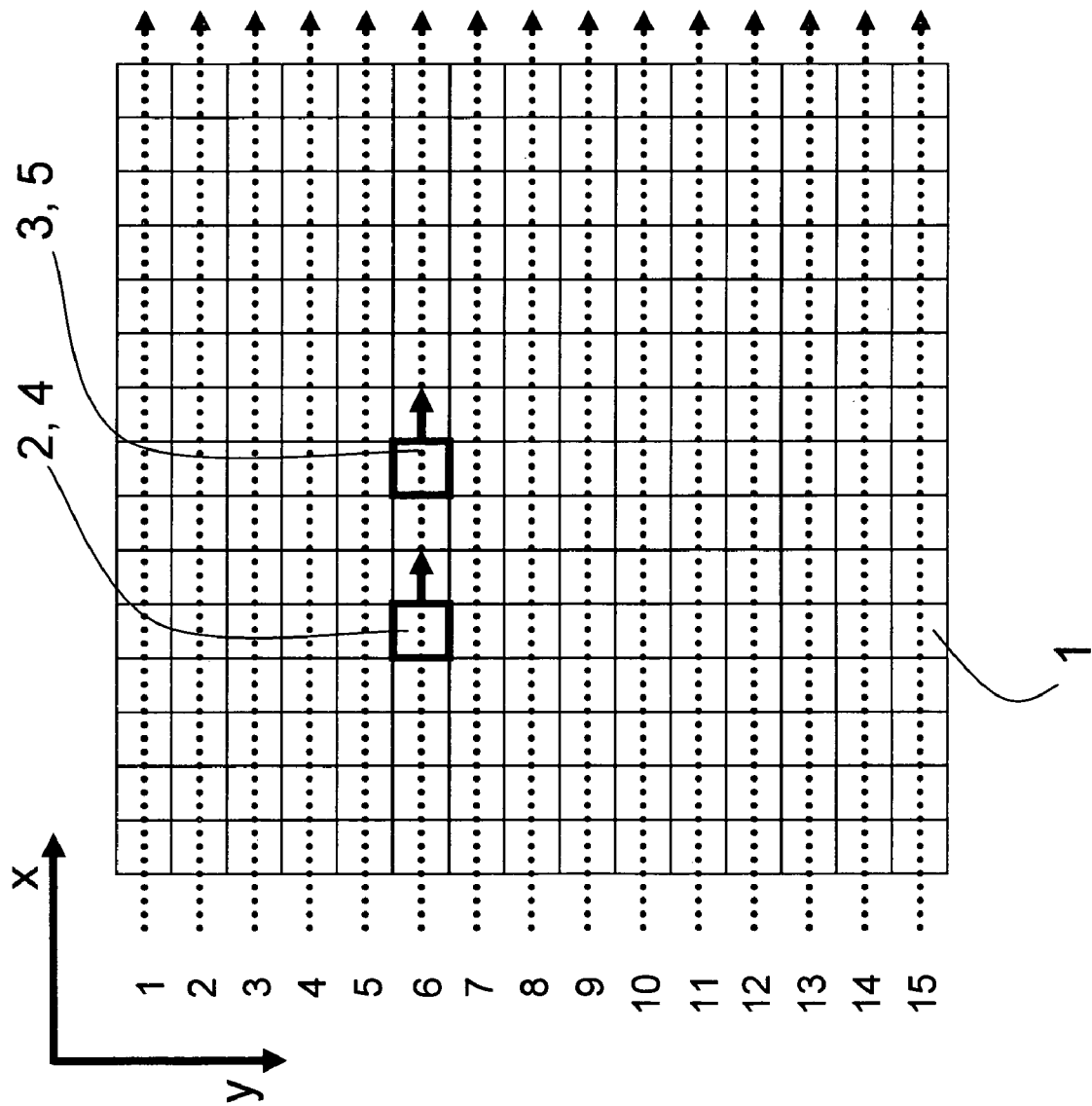
FIG. 1 schematically depicts the scanning operation according to a first exemplifying embodiment of a method according to the present invention for investigating transport processes.

FIG. 1, in which pixels 1 of a specimen are depicted in an X,Y coordinate system, schematically shows line-by-line scanning of the specimen with two laser light beams 2, 3, the one laser light beam 2 functioning as manipulation light beam 4 and the other laser light beam 3 as image production light beam 5. The two laser light beams 2, 3 are guided over the specimen along the positive X direction. When the end of a line is reached, the scanning operation is continued at the end of a line that follows in the Y scanning direction.

As is clearly evident from FIG. 1, two illumination points, at different locations on the specimen, are generated by laser light beams 2, 3. The two illumination points, which are indicated by a thicker border, possess a fixed physical distance from one another and scan the specimen synchronously with one another. The physical distance between the two illumination points is achieved by way of a definable angle difference between manipulation light beam 4 and image production light beam 5. Because image production light beam 5 precedes manipulation light beam 4, image production light beam 5 always sees a specimen that is as yet uninfluenced by manipulation light beam 4.

Figure 2:
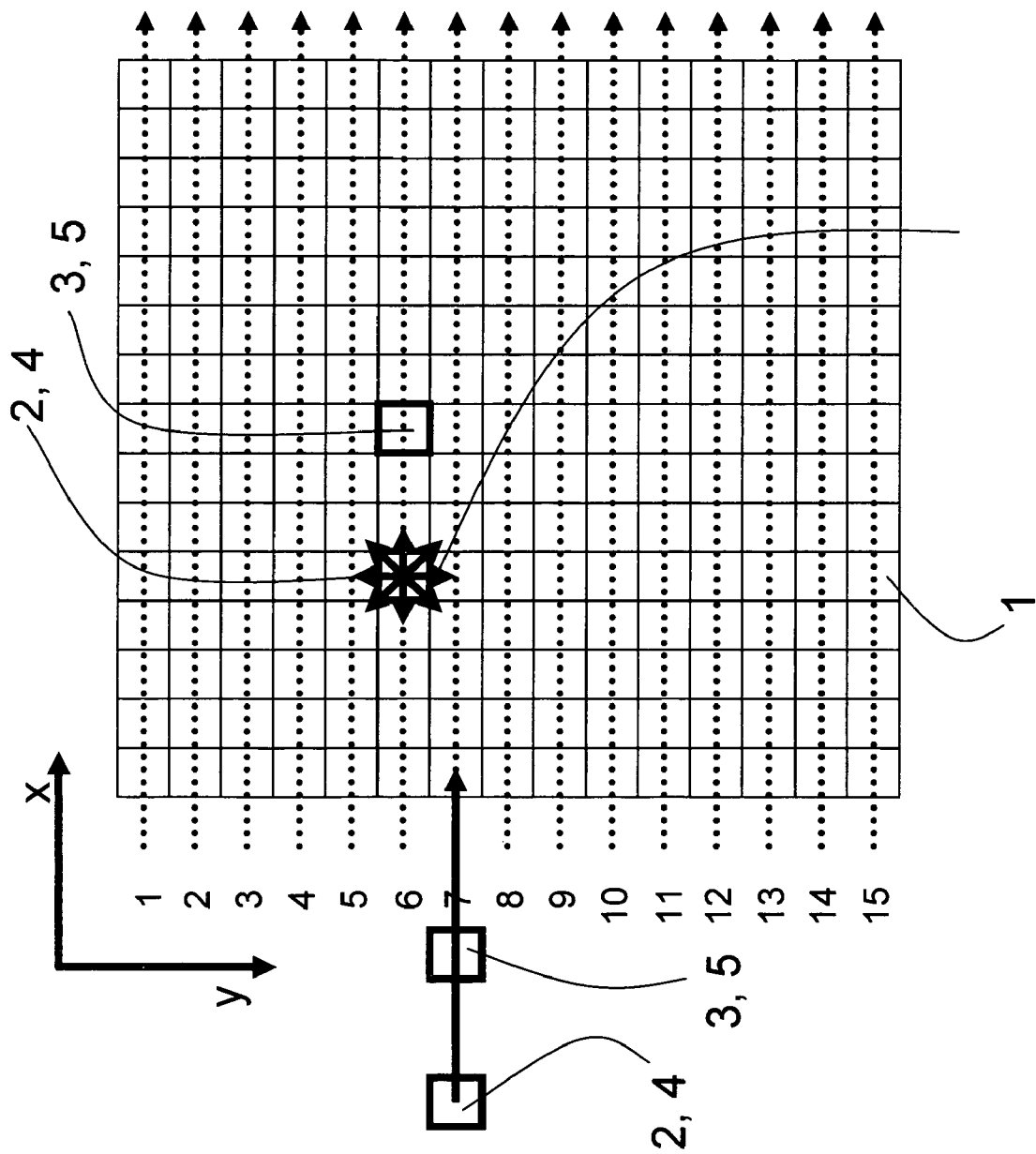
FIG. 2 depicts the scanning operation of FIG. 1 at a later point in time.

FIG. 2 schematically shows the same scanning operation as in FIG. 1, but at a more advanced point in time. Because the specimen has been influenced by manipulation light beam 4, transport processes take place in the pixels swept by manipulation light beam 4; among other effects, those processes cause fluorophores to be transported into adjacent pixels. This process is depicted schematically, with arrows, for one pixel in the line numbered 6. In the operation depicted in FIG. 2 in which the next line (numbered 7) is scanned, those fluorophores that were transported as a result of a transport process from a previous image line into the image line currently being imaged are now sensed by image production light beam 5 and thus made visible in the image. Because of the fixed angle difference between manipulation light beam 4 and image production light beam 5, in each line image production light beam 5 always has a fixed spacing in time from manipulation light beam 4 of the previous line which influenced the transported fluorophores. The method described can thus be used with particular advantage in conjunction with photoactivatable fluorophores. Utilization for FRAP, FLIP, or similar experiments is, however, additionally possible.

FIG. 3 shows, once again schematically, acquired images that can be obtained with the method according to the present invention. FIG. 3a), firstly, depicts a possible transport flow within the specimen. What is depicted specifically is a transport process that proceeds counterclockwise around a center. While no transport processes take place at the center itself, the intensity of the transport processes increases with increasing distance from the center.

The subsequent FIGS. 3b) to e) show the relevant acquired intensity images. FIG. 3b) shows an image that was obtained, as explained in conjunction with FIGS. 1 and 2, from a specimen scan in the positive X and positive Y direction. The bright left half of the image results from the strong transport flow in the positive Y direction in this region. The right half of the image, conversely, appears dark, since no transport flow in the positive Y direction is present in the corresponding specimen region.

FIG. 3c) shows an image rotated 90° by means of an image rotator. The bright upper region of the image is attributable to the transport flow in the negative X direction present in this specimen region. FIG. 3d) shows an acquired image rotated 180°, which was obtained with a Y scan direction turned around as compared with the image shown in FIG. 3b). A high intensity exists here in the right part of the image, attributable to the transport flow in the negative Y direction present in the corresponding specimen region. Lastly, FIG. 3e) shows an acquired image rotated 270°. This image was acquired using a 90° image rotator and a Y scanning direction as in the image depicted in FIG. 3d).

From the individual images, the transport flow in the interior of the specimen can easily be calculated, for example by determining the projection of the flow onto a fixed X or Y axis relative to the specimen by differentiating the intensity values in the 0° and 180° images and in the 90° and 270° images, respectively, thus yielding the relevant local vectors. Those vectors are depicted, as already explained above, in FIG. 3a). It is also possible in this fashion to detect local sinks and sources of the transport flow caused, inter alia, either by the production or annihilation of fluorophores or by transport into or out of the image plane. It may be noted that the method described need not necessarily be carried out in an image plane parallel to the specimen surface. Oblique sections through the specimen are likewise possible.

Figure 4:
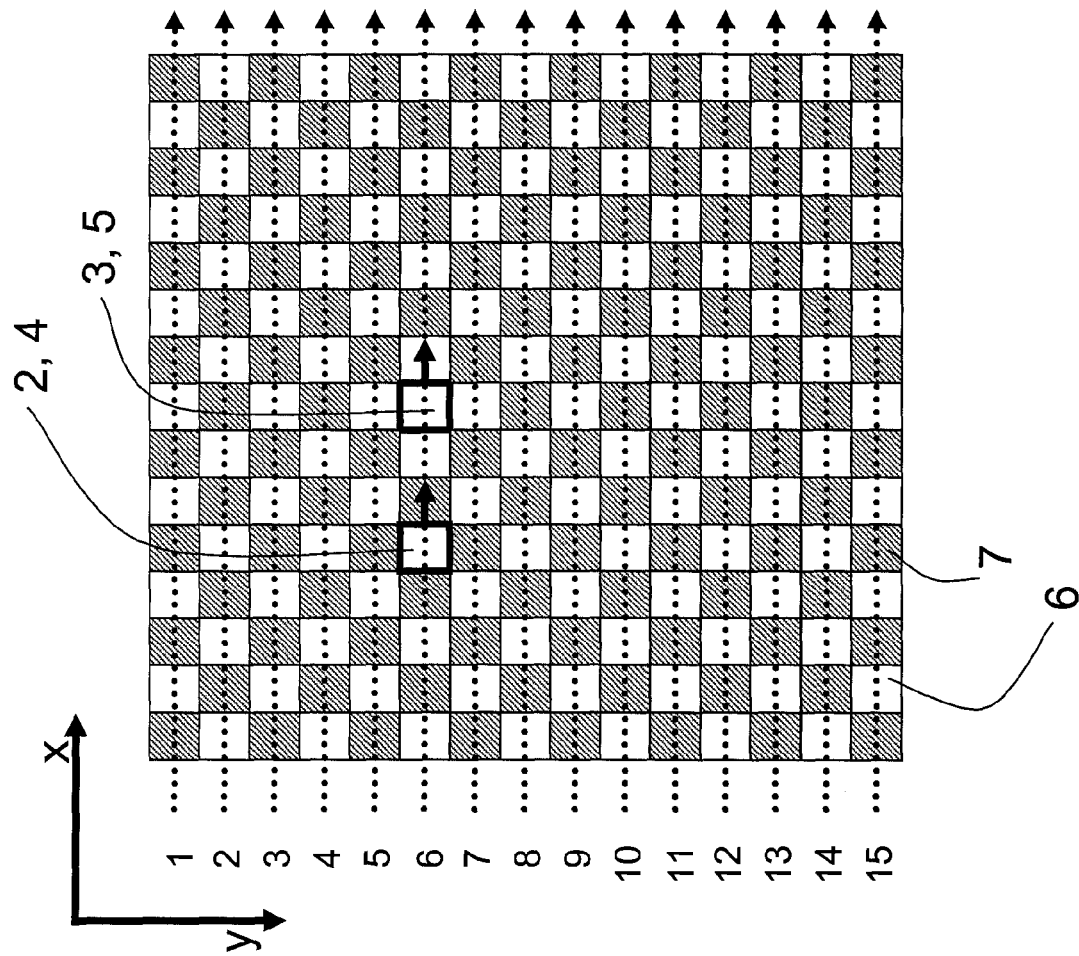
FIG. 4 schematically depicts the scanning operation according to a second exemplifying embodiment of a method according to the present invention.

Lastly, FIG. 4 schematically shows the scanning operation according to a further exemplifying embodiment of the method according to the present invention. Here manipulation light beam 4 is controlled in such a way that it alternately illuminates pixels 6 and exempts pixels 7 from illumination, the overall result being a manipulation illumination in the manner of a checkerboard. Apart from that, the reader is referred, in order to avoid repetition, to the statements made in conjunction with FIGS. 1 and 2.

In conclusion, be it noted very particularly that the exemplifying embodiments discussed above serve merely to describe the teaching claimed, but do not limit it to the exemplifying embodiments.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for investigating a transport flow in a specimen, comprising:
   scanning image production laser beam illumination line by line over the specimen within definable specimen regions;
   scanning manipulation laser beam illumination line-by-line over the specimen;
   illumination with the image production laser beam illumination preceding illumination with the manipulation laser beam illumination in such a way that pixels of the definable specimen regions are illuminated with the image production laser beam illumination before such pixels are illuminated by the manipulation laser beam illumination;
   producing an image of the specimen following illumination with the manipulation laser beam illumination; and
   calculating the transport flow from multiple images of the specimen each image of the multiple images being rotated with respect to one another by a definable angle.

2. The method according to claim 1, wherein calculating the transport flows comprises rotating each image of the multiple images by an image rotator or by activation of a scanning apparatus.

3. The method according to claim 1, wherein calculating the transport flows comprises acquiring multiple images for rotations of 0°, 90°, 180°, and 270°, respectively.

4. The method according to claim 1, wherein calculating the transport flows comprises acquiring multiple images for rotations of 0°, 120°, and 240°, respectively.

5. The method according to claim 1, wherein calculating the transport flow within the specimen comprises calculating linear combinations of the intensity values of the multiple images.

6. The method according to claim 1, wherein calculating the transport flow within the specimen comprises applying correction methods.

7. A method for investigating a transport flow in a specimen, comprising:
   scanning image production laser beam illumination line by line over the specimen within definable specimen regions;
   scanning manipulation laser beam illumination line-by-line over the specimen;
   illumination with the image production laser beam illumination preceding illumination with the manipulation laser beam illumination in such a way that pixels of the definable specimen regions are illuminated with the image production laser beam illumination before such pixels are illuminated by the manipulation laser beam illumination; and
   producing an image of the specimen following illumination with the manipulation laser beam illumination;
   wherein boundary lines or boundary surfaces are plotted in the image of the specimen; and
   wherein the transport flow through the boundary lines or the boundary surfaces is indicated quantitatively.

8. The method according to claim 1, wherein each line of the specimen is scanned twice, first by the image production laser beam illumination and then by the manipulation laser beam illumination.

9. The method according to claim 1, wherein each line of the specimen is scanned only once, the lines respectively being illuminated alternately for image production and for manipulation of the specimen.

10. The method according to claim 1, wherein illumination with the image production laser beam illumination precedes illumination with the manipulation laser beam illumination of the specimen by a fixed correlation in time.

11. The method according to claim 1, wherein a separate laser light beam is used to generate an image production laser light beam and a manipulation laser light beam.

12. The method according to claim 11, wherein the image production and the manipulation laser light beams exhibit a fixed angle difference with respect to one another.

13. The method according to claim 1, wherein the method is carried out by means of a confocal microscope.

14. The method according to claim 1, wherein a speed of the-scanning steps is adapted to a speed of the transport flow.

15. The method according to claim 1, wherein scanning the manipulation laser beam illumination over the specimen is confined to the definable specimen regions.

16. The method according to claim 1, wherein scanning the manipulation laser beam illumination along a line comprises illuminating the specimen continuously.

17. The method according to claim 1, wherein scanning the manipulation laser beam illumination along a line comprises illuminating the specimen is interrupted to occur in a checkerboard-like pattern.

18. The method according to claim 1, wherein the manipulation laser beam illumination is spectrally selective.

19. The method according to claim 1, further comprising detecting the light proceeding from the specimen as spectrally sensitive detection.

20. The method according to claim 1, wherein producing the image of the specimen comprises visualizing measured data via color codings, vector diagrams, or contour line graphs.

21. The method according to claim 1, wherein boundary lines or boundary surfaces are plotted in the image of the specimen.

* * * * *